(12) United States Patent
Yang et al.

(10) Patent No.: US 10,138,500 B2
(45) Date of Patent: Nov. 27, 2018

(54) D-LACTIC ACID-PRODUCING STRAIN AND USE THEREOF

(71) Applicant: CJ Cheiljedang Corporation, Seoul (KR)

(72) Inventors: Eun Bin Yang, Seoul (KR); Tae Hee Lee, Seongnam-si (KR); Seon Hye Kim, Bucheon-si (KR); Young Lyeol Yang, Goyang-si (KR); Hong Xian Li, Seoul (KR)

(73) Assignee: CJ CHEIJEDANG CORPORATION, Seoul (KR)

( * ) Notice: Subject to any disclaimer, the term of this patent is extended or adjusted under 35 U.S.C. 154(b) by 520 days.

(21) Appl. No.: 14/397,117

(22) PCT Filed: Apr. 24, 2013

(86) PCT No.: PCT/KR2013/003501
§ 371 (c)(1),
(2) Date: Oct. 24, 2014

(87) PCT Pub. No.: WO2013/162274
PCT Pub. Date: Oct. 31, 2013

(65) Prior Publication Data
US 2015/0118724 A1 Apr. 30, 2015

(30) Foreign Application Priority Data
Apr. 24, 2012 (KR) .......................... 10-2012-0042894

(51) Int. Cl.
*C12P 7/56* (2006.01)
*C12N 9/04* (2006.01)

(52) U.S. Cl.
CPC .............. *C12P 7/56* (2013.01); *C12N 9/0006* (2013.01); *C12Y 101/01027* (2013.01); *C12Y 101/01028* (2013.01)

(58) Field of Classification Search
CPC ...... C12N 9/0006; C12N 15/52; C12N 15/74; C12P 7/56; C12P 7/0006; C12Y 101/01027; C12Y 101/01028; C12R 1/07; C07C 59/08
See application file for complete search history.

(56) References Cited

U.S. PATENT DOCUMENTS

2004/0029256 A1    2/2004   Rajgarhia et al.

FOREIGN PATENT DOCUMENTS

| JP | H6-30781 A | 2/1994 |
| JP | H06-030781 A | 2/1994 |
| JP | 6085023 B2 | 2/2017 |
| KR | 10-1998-0086644 A | 12/1998 |

OTHER PUBLICATIONS

Taguchi et al (D-lactate dehydrogenase is a member of the D-isomer-specific 2-hydroxyacid dehydrogenase family. Cloning, sequencing, and expression in *Escherichia coli* of the D-lactate dehydrogenase gene of Lactobacillus plantarum J Biol Chem. Jul. 5, 1991;266 (19):12588-94 see attached).*
Decision of Rejection dated Jul. 5, 2016 in connection with Japanese Patent Application No. 2015-508862, filed Oct. 30, 2015.
Akira Manome, et al., "The ratio of l-form to d-form of lactic acid as a criteria for the identification of lactic acid bacteria", J. Gen. Appl. Microbiol., (1998), pp. 371-374, vol. 44 [6].
First Office Action, dated Nov. 10, 2015 in connection with Japanese Patent Application No. 2015-508862, filed Oct. 30, 2015.
Okano, K. et al. (2009). Efficient production of optically pure D-lactic acid from raw corn starch by using a genetically modified L-lactate dehydrogenase gene-deficient and α-amylase-secreting lactobacillus plantarum strain. *Applied and Environmental Microbiology*, 75(2), 462-467.
Okano, K. et al. (2009). Homo-D-lactic acid fermentation from arabinose by redirection of the phosphoketolase pathway to the pentose phosphate pathway in L-lactate dehydrogenase gene-deficient lactobacillus plantarum. *Applied and Environmental Microbiology*, 75(15), 5175-5178.
Ishida, N. et al. (2006). D-Lactic acid production by metabolically engineered *Saccharomyces cerevisiae*. *Journal of Bioscience and Bioengineering*, 101(2), 172-177.
Rico, J. et al. (2008). Analysis of ldh genes in *Lactobacillus casei* BL23: Role on lactic acid production. *J Ind Microbiol Biotechnol*, 35, 579-586.
Demirci, A. and Pometto III, A. L. (1992). Enhanced production of D(-)-lactic acid by mutants of *Lactobacillus delbrueckii* ATCC 9649*. *Journal of Industrial Microbiology*, 11, 23-28.
Notification of Transmittal of the International Search Report and the Written Opinion of the International Searching Authority, or the Declaration, including an International Search Report and Written Opinion of the International Searching Authority, dated Aug. 27, 2013 in connection with PCT International Application No. PCT/KR2013/003501, filed Apr. 24, 2013.
Feb. 12, 2016 official action in connection with Russian Patent Application No. 2014144647.
Okino et al. (2008), "Production of D-Lactic Acid by *Corynebacterium glutamicum* under Qxygen Deprivation", *Appl. Microbiol. Biotechnol.*, 78(3), 449-454 (English-language abstract only).
Office Action dated Nov. 14, 2017 by the JPO in connection with related Japanese Patent Application No. JP 2016216887.
Kenji Okano, et al., "Efficient Production of Optically Pure D-Lactic Acid from Raw Corn Starch by Using a Genetically Modified L-Lactate Dehydrogenase Gene-Deficient and α-Amylase-Secreting *Lactobacillus plantarum* Strain", Applied and Environmental Microbiology, Jan. 2009, pp. 462-467, American Society for Microbiology.

(Continued)

*Primary Examiner* — Kagnew H Gebreyesus
(74) *Attorney, Agent, or Firm* — John P. White; Cooper & Dunham LLP

(57) ABSTRACT

The present invention relates to a method for preparing a D-lactic acid-producing strain modified to inhibit L-lactate dehydrogenase (L-LDH) activity and to introduce D-lactate dehydrogenase (D-LDH) activity in an L-lactic acid-producing strain, a mutated D-lactic acid-producing strain prepared by the above method, and a method for producing D-lactic acid including the steps of culturing the strain and recovering D-lactic acid from the culture media.

21 Claims, 1 Drawing Sheet
Specification includes a Sequence Listing.

(56) References Cited

OTHER PUBLICATIONS

Nobuhiro Ishida, et al., "D-Lactic Acid Production by Metabolically Engineeered *Saccharomyces cerevisiae*", Journal of Bioscience and Bioengineering, 2006, vol. 101, No. 2, 172-177, The Society for Biotechnology, Japan.
Akira Manome, et al., "The ratio of L-form to D-form of lactic acid as a criteria for the identification of lactic acid bacteria", J. Gen. Appl. Microbiol., 1998, 44, 371-374.
Written Opinion dated Nov. 28, 2017 by the IPOS in connection with related Singaporean Patent Application No. SG 11201406876V.
Kenji Okano, et al., "Homo-D-Lactic Acid Fermentation from Arabinose by Redirection of the Phosphoketolase Pathway to the Pentose Phosphate Pathway in L-Lactate Dehydrogenase Gene-Deficient Lactobacillus plantarum", Applied and Environmental Microbiology, Aug. 2000, pp. 5175-5178, American Society of Microbiology.
Office Action dated Dec. 22, 2017 by the SIPO in connection with related Chinese Patent Application No. CN 201380033424.1 including English language translation.
Reference cited in Dec. 22, 2017 Chinese Office Action: 保加利亚乳杆菌代谢途径中关键基因的克隆与序列分析, 谭文籍, 中国优秀硕士学位论文全文数据库, 2011年S2期.

* cited by examiner

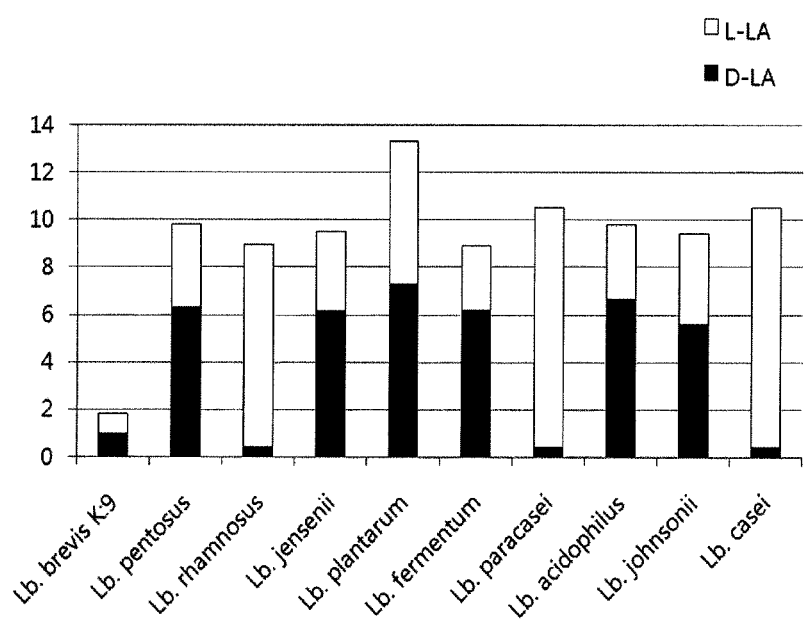

D-LACTIC ACID-PRODUCING STRAIN AND USE THEREOF

CROSS-REFERENCE TO RELATED APPLICATIONS

This application is a § 371 national stage of PCT International Application No. PCT/KR2013/003501, filed Apr. 24, 2013, claiming priority of Korean Patent Application No. 10-2012-0042894, filed Apr. 24, 2012, the contents of each of which are hereby incorporated by reference in their entirety.

BACKGROUND OF THE INVENTION

1. Field of the Invention

The present invention relates to a novel D-lactic acid-producing strain and a use thereof. Specifically, the present invention relates to a method for preparing a D-lactic acid-producing strain including the steps of inhibiting L-lactate dehydrogenase (L-LDH) activity and introducing D-lactate dehydrogenase (D-LDH) activity in an L-lactic acid-producing strain, a modified D-lactic acid-producing strain prepared by the above method, and a method for producing D-lactic acid including the steps of culturing the strain and recovering D-lactic acid from the culture broth.

2. Description of the Related Art

Lactic acid has a wide range of industrial applications in foods, medicines, cosmetics, etc. In recent years, lactic acid has been utilized as a monomer of polylactic acid, and thus there has been a remarkable increase in demand for lactic acid.

Lactic acid can be produced by the chemical synthesis or the biological fermentation process using carbohydrates as a substrate. The latter is preferred from a commercial point of view because the chemical synthesis of lactic acid creates a problem of the cost increase caused by the gas price increase or environmental contamination. In addition, there are also problems of producing L-lactic acid in the form of a racemic mixture consisting of an equal amount of D-lactic acid and L-lactic acid. Unfortunately, the composition ratio of the D-lactic acid and the L-lactic acid cannot be controlled. When lactic acid in the form of a racemic mixture is used for preparing polylactic acid, an amorphous polymer with a low melting point is produced, thus an application of it is limited. On the other hand, the biological fermentation process using microorganisms makes it possible to selectively produce D- or L-lactic acid depending on the strain used. For example, microorganisms such as *Lactobacillus* sp., *Bacillus* sp., *Rhizopus* sp., *Streptococcus* sp., or *Enterococcus* sp. usually produce L-lactic acid. Microorganisms such as *Leuconostoc* sp. and *Lactobacillus vulgaricus* usually produce D-lactic acid. In particular, due to D-lactic acid is not metabolized in the body, D-lactic acid can be used as a biomaterial in the medical field and also used as an optically active herbicide via esterification and chlorination. It has been known that an optically active herbicide, can considerably improve its pharmaceutical effect and also has the same pharmaceutical effect with a lesser amount. For this reason, a demand for D-lactic acid has been increasing. In addition, sc-polylactic acid (stereocomplex-PLA) has a significantly higher melting point and thermal degradation temperature than the known polylactic acids. Therefore, it can be used as a high heat-resistant plastic material, resulting from a mixture of pure L-polylactic acid and pure D-polylactic acid. Consequently, a monomer of D-lactic acid is needed, and its demand has been gradually growing.

In producing such optically pure D-lactic acid, the biological fermentation process using enantioselective substrate specificity of a microbial enzyme is preferred. However, the wild-type, D-lactic acid-producing microorganisms generally found in nature, are still not suitable for industrial use regarding of optical purity or productivity. Examples of the D-lactic acid-producing microorganisms are *Lb. plantarum, Lb. pentosus, fermentum, Lb delbrueckii*, or the like. However, there are disadvantages that they are not able to produce lactic acid with high productivity and high yield, and 20~40% of the lactic acid is L-lactic acid as an optical impurity. To overcome these disadvantages, attempts have been made to develop a variant producing high concentrations of lactic acid in a high glucose medium by inducing mutations in lactic acid-producing bacteria with treatment of EMS (ethyl methanesulfonate) (*J. Industrial Microbiol*, 11:23-28, 1992). As a result, the strain showing about a 4.8-fold higher productivity than a control group was selected, but its activity was reduced during long-term storage. Meanwhile, in the case of strain development using a variant, a yield-improved strain tends to show reduced productivity, whereas a productivity-improved strain tends to show reduced yield.

Based on the idea that strains for industrial lactic acid fermentation are generally L-lactic acid-producing microorganisms, and these microorganisms have mostly superior productivity and yield compared to D-lactic acid-producing microorganisms, the present inventors found that D-lactic acid can be produced in high yield by inactivating an L-lactate dehydrogenase (L-LDH)-encoding gene in a high L-lactic acid-producing microorganism and then introducing a heterogenous D-lactate dehydrogenase (D-LDH)-encoding gene thereto, thereby completing the present invention.

SUMMARY OF THE INVENTION

An embodiment of the present invention provides a method for preparing a modified D-lactic acid-producing strain, including the steps of attenuating or inactivating L-lactate dehydrogenase activity and introducing or enhancing D-lactate dehydrogenase activity in an L-lactic acid-producing strain.

Other embodiment of the present invention provides a modified D-lactic acid-producing strain that is prepared by the above method.

Another embodiment of the present invention provides a method for producing D-lactic acid using the modified D-lactic acid-producing strain.

BRIEF DESCRIPTION OF THE DRAWINGS

FIG. 1 shows a graph representing the results of analyzing a ratio of D-lactic acid and L-lactic acid produced by 10 different types of wild-type lactic acid-producing microorganisms.

DETAILED DESCRIPTION OF THE PREFERRED EMBODIMENTS

An embodiment of the present invention provides a method for preparing a modified D-lactic acid-producing strain by attenuating or inactivating L-lactate dehydrogenase (L-LDH) activity and introducing or enhancing D-lactate dehydrogenase (D-LDH) activity in an L-lactic acid-producing strain.

In detail, the method for preparing the modified D-lactic acid-producing strain of the present invention includes (a)

attenuating or inactivating L-lactate dehydrogenase (L-LDH) activity in an L-lactic acid-producing strain to obtain a modified lactic acid-producing strain; and (b) introducing or enhancing D-lactate dehydrogenase (D-LDH) activity in the modified lactic acid-producing strain.

In this regard, the L-lactic acid-producing strain may be a strain expressing only an L-LDH-encoding polynucleotide to produce L-lactic acid or a strain expressing an L-LDH-encoding polynucleotide and a D-LDH-encoding polynucleotide at the same time to produce both L-lactic acid and D-lactic acid. The method for attenuating or inactivating L-LDH activity may be carried out by substituting, deleting, inserting or adding one or several nucleotides at one or more positions of the L-LDH-encoding polynucleotide. The method for introducing or enhancing D-LDH activity may be carried out by introducing the D-LDH-encoding polynucleotide into the chromosome of the modified lactic acid-producing strain, introducing a polynucleotide encoding a D-LDH variant having improved activity into the chromosome of the modified lactic acid-producing strain, introducing a strong promoter into upstream of the D-LDH-encoding polynucleotide in the chromosome of the mutated lactic acid-producing strain, introducing a strong promoter and the D-LDH-encoding polynucleotide operably linked to the promoter into the chromosome of the modified lactic acid-producing strain, introducing a strong promoter and the polynucleotide encoding the D-LDH variant having improved activity, which is operably linked to the promoter, into the chromosome of the modified lactic acid-producing strain, introducing an expression vector including the D-LDH-encoding polynucleotide into the modified lactic acid-producing strain, introducing an expression vector including the polynucleotide encoding the D-LDH variant having improved activity into the modified lactic acid-producing strain, introducing an expression vector including a strong promoter and the D-LDH-encoding polynucleotide operably linked to the promoter into the modified lactic acid-producing strain, introducing an expression vector including a strong promoter and the polynucleotide encoding the D-LDH variant having improved activity, which is operably linked to the promoter, into the modified lactic acid-producing strain, or the like.

As used herein, the term "lactate dehydrogenase (LDH)" refers to an enzyme that catalyzes production of pyruvate from lactate by removal of hydrogen or production of lactate from pyruvate by reduction using NADH. LDH has a molecular weight of about 140 kDa, and can be classified into L-LDH (EC 1.1.1.27.) producing L-lactic acid, D-LDH (EC 1.1.1.28.) producing D-lactic acid, and L-LDH (cytochrome b2, EC 1.1.2.3) containing FMN and heme.

As used herein, the term "L-lactic acid-producing strain" refers to a strain that expresses an L-LDH-encoding polynucleotide and produces L-lactic acid using the expressed L-LDH. In addition, the strain also includes a strain that produce both L-lactic acid and D-lactic acid by expressing the L-LDH-encoding polynucleotide and D-LDH-encoding polynucleotide at the same time as a strain that produce L-lactic acid by expressing only the L-LDH-encoding polynucleotide. The L-lactic acid-producing strain is not particularly limited, as long as it can produce L-lactic acid. For example, *Lactobacillus brevis*, *Lactobacillus pentosus*, *Lactobacillus rhamnosus*, *Lactobacillus jensenii*, *Lactobacillus plantarum*, *Lactobacillus paraplantarum*, *Lactobacillus fermentum*, *Lactobacillus paracasei*, *Lactobacillus acidophilus*, *Lactobacillus johnsonii*, and *Lactobacillus casei* may be used, specifically, *Lactobacillus rhamnosus*, *Lactobacillus paracasei*, and *Lactobacillus casei* may be used, and more specifically *Lactobacillus paracasei* may be used.

The method for attenuating or inactivating L-LDH activity in the L-lactic acid-producing strain may be carried out using a method known in the art. For example, a method for inhibiting expression of the L-LDH-encoding polynucleotide or producing inactivated L-LDH may be a method for substituting, deleting, inserting or adding one or several nucleotides, specifically 2 to 20 nucleotides, more specifically, 2 to 10 nucleotides, and further more specifically 2 to 5 nucleotides of the L-LDH-encoding polynucleotide inherent in the L-lactic acid-producing strain. In addition, any method may be used without particular limitation, as long as it is used to attenuate or inactivate L-LDH activity in the L-lactic acid-producing strain.

In the present invention, L-LDH to be attenuated or inactivated may inherent in the L-lactic acid-producing strain. The amino acid sequence of the L-LDH or the polynucleotide sequence encoding the same is not particularly limited. The L-LDH may be represented by a polynucleotide sequence (SEQ ID NO: 25) encoding LDH and a polynucleotide sequence (SEQ ID NO: 26) encoding LDH1 of *Lactobacillus paracasei*, a polynucleotide sequence (SEQ ID NO: 27) encoding LDH1 and a polynucleotide sequence (SEQ ID NO: 28) encoding LDH2 of *Lactobacillus casei*, a polynucleotide sequence (SEQ ID NO: 29) encoding LGG_02523 and a polynucleotide sequence (SEQ ID NO: 30) encoding LGG_00606 of *Lactobacillus rhamnosus*.

As used herein, the term "modified lactic acid-producing strain" refers to an L-lactic acid-producing strain of which L-LDH activity is attenuated or inactivated. The lactic acid-producing strain may be modified to attenuate or inactivate L-LDH activity by inducing artificial mutations in the normal L-lactic acid-producing strain, or by naturally occurring mutations without inducing artificial mutations.

The method for introducing or enhancing D-LDH activity in the modified lactic acid-producing strain may be, but is not particularly limited to, a method for introducing the D-LDH-encoding polynucleotide into the chromosome of the modified lactic acid-producing strain, a method for introducing a polynucleotide encoding a D-LDH variant having improved activity into the chromosome of the mutated lactic acid-producing strain, a method for introducing a strong promoter into upstream of the D-LDH-encoding polynucleotide in the chromosome of the modified lactic acid-producing strain, a method for introducing a strong promoter and the D-LDH-encoding polynucleotide operably linked to the promoter into the chromosome of the modified lactic acid-producing strain, a method for introducing a strong promoter and the polynucleotide encoding the D-LDH variant having improved activity, which is operably linked to the promoter, into the chromosome of the modified lactic acid-producing strain, a method for introducing an expression vector including the D-LDH-encoding polynucleotide into the modified lactic acid-producing strain, a method for introducing an expression vector including the polynucleotide encoding the D-LDH variant having improved activity into the modified lactic acid-producing strain, a method for introducing an expression vector including a strong promoter and the D-LDH-encoding polynucleotide operably linked to the promoter into the modified lactic acid-producing strain, a method for introducing an expression vector including a strong promoter and the polynucleotide encoding the D-LDH variant having improved activity, which is operably linked to the promoter, into the modified lactic acid-producing strain, or the like.

As used herein, the term "expression vector" refers to a DNA product comprising a nucleotide sequence of a polynucleotide encoding a target protein, which is operably linked to a suitable regulatory sequence to express the polynucleotide encoding the target protein in a suitable host. The regulatory sequence may include a promoter capable of initiating transcription, an arbitrary operator sequence for regulating transcription, a sequence encoding an appropriate mRNA ribosome binding site, and sequences for regulating the termination of transcription and translation. Once a vector is transformed into a suitable host, the vector may replicate and function independently of the host genome, or may be integrated into the genome itself.

As long as it is replicable in hosts, any vector known in the art may be used as the expression vector in the present invention, without particular limitations. Example of the expression vector typically used may include a natural or recombinant plasmid, cosmid, virus and bacteriophage. Example of the phage vector or the cosmid vector may include pWE15, M13, λMBL3, λMBL4, λIXII, λASHII, λAPII, λt10, λt11, Charon4A, and Charon21A. The plasmid vector may include pBR type, pUC type, pBluescriptII type, pGEM type, pTZ type, pCL type, pET type, etc.

In detail, the vector used in embodiments of the present invention is pG+host6 which is a vector used in a wide range of Gram-positive bacteria. This vector is characterized in that it contains an ampicillin-resistant gene and a replication origin for use in *E. coli*, an erythromycin-resistant gene and a replication origin for use in Gram-positive bacteria. In particular, the replication origin in Gram-positive bacteria contains a heat-sensitive mutation, and therefore, replication does not occur at a temperature above 37° C. Therefore, it allows gene insertion via a homologous sequence in Gram-positive bacteria (US Patent Application Publication No. 20060025190).

As used herein, the term "transformation" means a series of operations of introducing a vector including a polynucleotide encoding a target protein into a host cell, expressing the polynucleotide in the host cell, and producing an expression product, mRNA or protein. The polynucleotide to be introduced into the host cell may be in any form, as long as it can be introduced into the host cell and expressed therein. For example, the polynucleotide may be introduced into a host cell in the form of an expression cassette that is a structure including all elements (a promoter operably linked to the polynucleotide, a transcription termination signal, a ribosome binding site, a translation termination signal, etc.) required for self-expression. The expression cassette may be in the form of a self-replicable expression vector. In addition, the polynucleotide itself may be introduced into a host cell to be operably linked to a sequence required for expression in the host cell.

D-LDH used in the present invention may be, but is not particularly limited to, derived from a strain producing D-lactic acid. Specifically derived from *Lactobacillus plantarum* or *Lactobacillus delbrueckii*, and further more specifically, a polypeptide represented by an amino acid sequence of SEQ ID NO: 31 of *Lactobacillus delbrueckii* or an amino acid sequence of SEQ ID NO: 32 of *Lactobacillus plantarum*. In addition, substitution, deletion, insertion, addition or inversion of one amino acid or several amino acids (may be depending on positions of amino acid residues in the three-dimensional structure of the protein or types of the amino acid residues, specifically 2 to 20, more specifically 2 to 10, further more specifically 2 to 5 amino acids) at one or more positions of amino acid sequence of SEQ ID NO: 31 or 32, may be included. As long as it can maintain or enhance the D-LDH activity, an amino acid sequence having 80% or more, specifically 90% or more, more specifically 55% or more, further more specifically 97% or more homology with the amino acid sequence of SEQ ID NO: 31 or 32 may be included. Since the amino acid sequence of the enzyme may be different depending on the species or the strain of a microorganism, the substitution, deletion, insertion, addition or inversion of the amino acid also includes a naturally occurring mutated sequence or an artificially mutated sequence, but is not particularly limited thereto.

As used herein, the term "homology" refers to identity between two different amino acid sequences or two different nucleotide sequences, and can be determined by a method well known to those skilled in the art. For example, BLAST 2.0 calculating parameters such as score, identity, and similarity may be used, but is not particularly limited thereto.

Generally, the L-lactic acid-producing strain produces lactic acid with a higher production yield than the D-lactic acid-producing strain. Thus, the present inventors intended to prepare a strain having excellent D-lactic acid producibility by modifying the L-lactic acid-producing strain to the D-lactic acid-producing strain. To this end, the fermentation ratio of D- and L-lactic acids was compared between the wild-type *LactoBacillus* sp. strains. As a result, it was found that *Lactobacillus paracasei*, *Lactobacillus casei* and *Lactobacillus rhamnosus* strains showed excellent overall producibility of lactic acid, and their L-lactic acid ratios were overwhelmingly excellent. Therefore, the present inventors intended to prepare modified strains thereof (FIG. 1). For example, ldh and ldh1 genes of L-LDHin *Lactobacillus paracasei* were deleted, and at the same time, δldh1-ldhA (Lb. db) and δldh-ldhD(Lb. pl) as the cassettes for D-LDH insertion were prepared, and then each of them was introduced into the heat-sensitive vector pG+host6 to prepare two types of vectors, pG+host6-δldh1-ldhA(Lb. db) and pG+host6-δldh-ldhD(Lb. pl) (Example 3). Subsequently, each vector was introduced into L-LDH gene-deleted *Lactobacillus paracasei* to prepare a transformant modified to attenuate or inactivate L-LDH activity and to enhance D-LDH activity (Example 4). Thus the prepared transformants were cultured, and lactic acid produced therefrom was analyzed. As a result, D-lactic acid was produced at a concentration of 41.6 g/L, but no L-lactic acid was produced. The production yield of D-lactic acid produced in the present invention was higher than that of D-lactic acid produced by the known D-lactic acid-producing strain (Example 5).

Accordingly, when L-LDH activity is attenuated or inactivated and D-LDH activity is introduced or enhanced in the L-lactic acid-producing strain having high production yield of lactic acid, D-lactic acid can be produced in higher yield than c the known D-lactic acid-producing strains.

An embodiment of the present invention provides a D-lactic acid-producing strain modified to attenuate or inactivate the L-LDH activity and to introduce or enhance the D-LDH activity in the L-lactic acid-producing strain showing the L-LDH activity using the above method.

The modified D-lactic acid-producing strain may be a strain in which the D-LDH-encoding polynucleotide is substituted for the L-LDH-encoding polynucleotide in the chromosome of L-lactic acid-producing strain or is overexpressed. The modified D-lactic acid-producing strain, although not particularly limited, may be a strain in which a polynucleotide encoding LDH1 (SEQ ID NO: 27) and a polynucleotide encoding LDH2 (SEQ ID NO: 28) of *Lactobacillus casei* are substituted with a polynucleotide encoding LDHA (SEQ ID NO: 31) of *Lactobacillus delbrueckii* and a polynucleotide encoding LDHD (SEQ ID NO: 32) of *Lactobacillus plantarum*, respectively; a strain in which a polynucleotide encoding LDH (LGG_02523) (SEQ ID NO: 29) and a polynucleotide encoding LDH (LGG_00606) (SEQ ID NO: 30) of *Lactobacillus rhamnosus* are substituted with a polynucleotide encoding LDHA (SEQ ID NO: 31) of *Lactobacillus delbrueckii* and a polynucleotide encoding LDHD (SEQ ID NO: 32) of *Lactobacillus plantarum*, respectively; a strain in which a polynucleotide encoding LDH (SEQ ID NO: 25) and a polynucleotide encoding LDH1 (SEQ ID NO: 26) of *Lactobacillus paracasei* are substituted with a polynucleotide encoding LDHA (SEQ ID NO: 31) of *Lactobacillus delbrueckii* and a polynucleotide encoding LDHD (SEQ ID NO: 32) of *Lactobacillus plantarum*, respectively. Specifically, The modified D-lactic acid-producing strain may be a strain in which a polynucleotide encoding LDH (SEQ ID NO: 25) and a polynucleotide encoding LDH1 (SEQ ID NO: 26) of *Lactobacillus paracasei* are substituted with a polynucleotide encoding LDHA (SEQ ID NO: 31) of *Lactobacillus delbrueckii* and a polynucleotide encoding LDHD (SEQ ID NO: 32) of *Lactobacillus plantarum*, respectively, and more specifically, *Lactobacillus paracasei* CC02-0095 (KCCM11273P).

The present inventors produced D-lactic acid using each of the transformants which were modified to delete each of the L-LDH-encoding polynucleotides in *Lactobacillus paracasei, Lactobacillus casei* and *Lactobacillus rhamnosus* strains and to introduce the polynucleotide encoding LDHA (SEQ ID NO: 31) of *Lactobacillus delbrueckii* and the polynucleotide encoding LDHD (SEQ ID NO: 32) of *Lactobacillus plantarum*, respectively into them. The yield, productivity, production amount, etc., of the D-lactic acid were compared. As a result, it was confirmed that the transformant derived from *Lactobacillus paracasei* (*Lb. paracasei* ldh::ldhA ldh1::ldhD) was the most excellent in terms of yield, productivity, and production amount of the D-lactic acid.

Accordingly, the present inventors designated the transformant (*Lb. paracasei* ldh::ldhA ldh1::ldhD) as *Lactobacillus paracasei* CC02-0095, in which the transformant was the most excellent in terms of yield, productivity, and production amount of the D-lactic acid. The CC02-095 was a strain prepared by substituting the polynucleotide encoding LDH (SEQ ID NO: 25) and the polynucleotide encoding LDH1 (SEQ ID NO: 26) of *Lactobacillus paracasei* with the polynucleotide encoding LDHA (SEQ ID NO: 31) of *Lactobacillus delbrueckii* and the polynucleotide encoding LDHD (SEQ ID NO: 32) of *Lactobacillus plantarum*. The transformant was deposited with the Korean Culture Center of Microorganisms (hereinafter, abbreviated to "KCCM") under the Budapest Treaty on Apr. 2, 2012 under Accession No. KCCM11273P.

Another embodiment of the present invention provides a method for producing D-lactic acid, including the steps of (a) culturing the modified D-lactic acid-producing strain to obtain a culture broth; and (b) recovering D-lactic acid from the culture broth.

The modified D-lactic acid-producing strain of the present invention is a strain prepared from an L-lactic acid-producing strain having excellent lactic acid producibility in order to make the strain produce D-lactic acid. Therefore, when the modified D-lactic acid-producing strain is cultured, D-lactic acid produced may be accumulated within the strain or in the culture medium. Consequently, D-lactic acid may be obtained by recovering the D-lactic acid that is accumulated within the cultured strain or in the culture medium.

As used herein, the term "culture" means all of the actions to grow a microorganism under moderately controlled artificial environmental conditions. In the present invention, the culture is conducted for the purpose of producing D-lactic acid from the modified D-lactic acid-producing strain, and a specific method for the culture is not particularly limited, as long as it can produce D-lactic acid from the modified D-lactic acid-producing strain. It can be conducted using any method widely known in the art. Specifically, it can be conducted by a batch process, a fed batch process or a continuous process.

Specifically, the medium used for the culture may have to meet the requirements of a specific strain in a proper manner while controlling temperature, pH, etc. under aerobic conditions in a typical medium containing a proper carbon source, nitrogen source, amino acids, vitamins, etc. Possible carbon sources may include a mixture of glucose and xylose as a main carbon source, sugars and carbohydrates such as sucrose, lactose, fructose, maltose, starch, and cellulose, oils and fats such as soy bean oil, sunflower oil, castor oil, and coconut fat, fatty acids such as palmitic acid, stearic acid, and linoleic acid, alcohols such as glycerol and ethanol, and organic acids such as acetic acid. These substances may be used alone or in combination. Possible nitrogen sources may include inorganic nitrogen sources such as ammonia, ammonium sulfate, ammonium chloride, ammonium acetate, ammonium phosphate, ammonium carbonate and ammonium nitrate; amino acids such as glutamic acid, methionine, and glutamine; and organic nitrogen sources such as peptone, NZ-amine, meat extract, yeast extract, malt extract, corn steep liquor, casein hydrolysates, fish or decomposition products thereof, and defatted soybean cake or decomposition products thereof. These nitrogen sources may be used alone or in combination. The medium may include potassium dihydrogen phosphate, dipotassium hydrogen phosphate or the corresponding sodium-containing salts as phosphorus sources. Possible phosphorus sources may include potassium dihydrogen phosphate, dipotassium hydrogen phosphate or the corresponding sodium-containing salts. Further, inorganic compounds such as sodium chloride, calcium chloride, iron chloride, magnesium sulfate, iron sulfate, manganese sulfate and calcium carbonate may be used. In addition to the above substances, essential growth substances, such as amino acids and vitamins, may be included. Appropriate precursors may be also added to the culture media. The above-mentioned substances may be suitably added to the culture medium in batch, fed-batch or continuous mode during cultivation, but are not particularly limited thereto. The pH of the culture may be adjusted by suitably adding basic compounds such as sodium hydroxide, potassium hydroxide, and ammonia, or acidic compounds such as phosphoric acid and sulfuric acid.

An anti-foaming agent such as fatty acid polyglycol esters may be used to suppress the development of foam. In order to maintain aerobic condition, oxygen or oxygen-containing gas (e.g., air) is introduced into the culture broth. The temperature of the culture broth is normally 27° C. to 37° C., specifically 30° C. to 35° C. The culture may be continued until the production of D-lactic acid reaches a desired level, and may be normally continued for 10 to 100 hours. D-lactic acid may be released into the culture medium or included within the cells.

Furthermore, recovering D-lactic acid from the culture broth may be performed by a known method known in the art. Specifically, the known method for recovering D-lactic acid is not particularly limited, as long as the method can recover D-lactic acid in the culture broth. Specifically, centrifugation, filtration, extraction, spraying, drying, evaporation, precipitation, crystallization, electrophoresis, fractional dissolution (e.g., ammonium sulfate precipitation, etc.), or chromatography (e.g., ion exchange chromatography, affinity chromatography, hydrophobic chromatography, and size exclusion chromatography, etc.) may be used.

Hereinafter, the present invention will be described in more detail with reference to Examples. However, these Examples are for illustrative purposes only, and the invention is not intended to be limited by these Examples.

Example 1: Analysis of Fermentation Ratio of D- and L-Lactic Acids of Wild-Type LactoBacillus sp. Strain Each of 10 types of wild-type lactic acid-producing strains was inoculated in 50 ml of GY medium (5% dextrose, 1% yeast extract, 0.05% sodium citrate, 3% CaCO$_3$, 0.02% MgSO$_4$, 0.001% MnSO$_4$, 0.001% FeSO$_4$ and 0.001% NaCl) and then cultured under anaerobic conditions at 37° C. for 40 hours, followed by HPLC analysis for a ratio of D-lactic acid and L-lactic acid in the fermentation broth (FIG. 1). FIG. 1 shows a graph representing the results of analyzing a ratio of D-lactic acid and L-lactic acid which were produced by 10 types of wild-type lactic acid-producing strains.

*Lactobacillus paracasei*, *Lactobacillus casei* and *Lactobacillus rhamnosus* showing high productivity of lactic acid and much higher ratio of L-lactic acid were selected from 10 types of the strains. The selected strains were modified to produce D-lactic acid.

Example 2: Comparison of Nucleotide Sequences of L-Lactate Dehydrogenase (L-LDH)

To delete a gene inducing overproduction of L-lactic acid in each of the strains selected in Example 1, homology between L-LDH-encoding gene of the selected strains was compared and analyzed by searching U.S. National Center for Biotechnology Information (NCBI) (www.ncbi.nlm.nih.gov) (Table 1).

TABLE 1

Homology comparison between L-LDH gene of *Lactobacillus paracasei* and homologous genes

| Homology with ldh of *Lactobacillus paracasei* | Homology with ldh1 of *Lactobacillus paracasei* |
|---|---|
| *Lactobacillus casei* ldh1 100% | *Lactobacillus casei* ldh2 99% |
| *Lactobacillus rhamnosus* ldh (LGG_02523) 91% | *Lactobacillus rhamnosus* ldh (LGG_00606) 79% |

As shown in Table 1, the L-LDH-encoding genes of 3 types of lactic acid-producing strains have very similar nucleotide sequences to each other, and in particular, ldh1 of *Lactobacillus casei* is known as an important L-lactic acid-producing gene (*J. Ind. Microbiotechnol.*, 2008, 35:579-586). Meanwhile, ldh2 of *Lactobacillus casei* is another L-lactic acid-producing gene. The ldh1 and ldh2 genes were deleted to prepare a strain producing optically pure D-lactic acid. In summary, from the total 3 types of parent strains, ldh and ldh1 genes of *Lactobacillus paracasei*, ldh1 and ldh2 genes of *Lactobacillus casei*, and 2 types of ldh genes of *Lactobacillus rhamnosus* were selected as genes for deletion.

Example 3: Construction of L-LDH-Deletion/D-LDH-Insertion Vectors

Vectors for deletions of the L-LDH genes of *Lactobacillus paracasei*, *Lactobacillus casei* and *Lactobacillus rhamnosus*, which were selected in Example 2, were prepared. In order to prepare a cassette for deleting L-LDH and inserting D-LDH at the same time, sequences adjacent to ORF of ldh and ldh1 of *Lactobacillus paracasei*, ldh1 and ldh2 of *Lactobacillus casei*, and LGG02523 and LGG00606 of *Lactobacillus rhamnosus* were used as homologous nucleotide sequence, and primers of SEQ ID NOs. 1 to 24 were prepared (Table 2).

TABLE 2

Nucleotide sequence of primer

| SEQ ID NO: | Nucleotide sequence (5'-3') | Template |
|---|---|---|
| 1 | atatgcctcgagcgggatttc ctaggccaacaatcat | Lb. paracasei, Lb. casei |
| 2 | ttgcgtaagcaaaaattttag tcatggtgatatcatcctttc ttatgtgc | Lb. paracasei, Lb. casei |
| 3 | gcacataagaaaggatgatat caccatgactaaaatttttgc ttacgcaa | Lb. delbrueckii |
| 4 | tggttgcttacttatcagtga tcgtgatgattagccaacctt aactggagtttca | Lb. delbrueckii |
| 5 | tgaaactccagttaaggttgg ctaatcatcacgatcactgat aagtaagcaacca | Lb. paracasei, Lb. casei |
| 6 | atatgcactagtgcttgttaa ggatttgtgtcaagcctt | Lb. paracasei, Lb. casei |
| 7 | atctctcgagtctgacttacc tttcggatcaaaat | Lb. paracasei, Lb. casei |
| 8 | ctcaaattcctcctcatgaag atct | Lb. paracasei, Lb. casei |
| 9 | cgtcaagatcttcatgaggag gaatttgagatgaaaattatt gcatatgc | Lb. plantarum |
| 10 | ccgttaagctgagcgcttaac ctgacgagcttagtcaaactt aacttgcg | Lb. plantarum |
| 11 | gctcgtcaggttaagcgctca gctt | Lb. paracasei, Lb. casei |
| 12 | atatactagtccgttggctgg gcattgcgtcattc | Lb. paracasei, Lb. casei |
| 13 | cccctcgagctggtaataca tcattaactgccgc | Lb. rhamnosus |
| 14 | ttgcgtaagcaaaaattttag tcatggtgatatcatcctttc ttatgtgc | Lb. rhamnosus |
| 15 | gcacataagaaaggatgatat caccatgactaaaatttttgc ttacgcaa | Lb. delbrueckii |
| 16 | ggtttaaaatcagttatggtg aagattagccaaccttaactg gagtttca | Lb. delbrueckii |

TABLE 2-continued

Nucleotide sequence of primer

| SEQ ID NO: | Nucleotide sequence (5'-3') | Template |
|---|---|---|
| 17 | tgaaactccagttaaggttgg ctaatcttcaccataactgat tttaaacc | Lb. rhamnosus |
| 18 | tagaactagtttattcagcac ttgagtaagtcctt | Lb. rhamnosus |
| 19 | cccctcgagaaccaagcgtc caagaatgtttgct | Lb. rhamnosus |
| 20 | gtacagcatatgcaataattt tcatcctaaaccctccttga caggtagc | Lb. rhamnosus |
| 21 | gctacctgtcaaggaggggtt taggatgaaaattattgcata tgctgtac | Lb. plantarum |
| 22 | aaaaatactgacgatgggttg tgttttagtcaaacttaactt gcgtatca | Lb. plantarum |
| 23 | tgatacgcaagttaagtttga ctaaaacacaacccatcgtca gtattttt | Lb. rhamnosus |
| 24 | tagaactagtcaaccgttgtc gaaagcattgcggt | Lb. rhamnosus |

The sequence of 700 base pairs at 5' region (ldh.pc_UP_700) and the sequence of 700 base pairs at 3' region (ldh.pc_DOWN_700) of ldh gene ORF were amplified using the genome of *Lactobacillus paracasei* as a template and primers of SEQ ID NOS. 1 and 2, and primers of SEQ ID NOS: 5 and 6. The sequence of 700 base pairs at 5' region (ldh1.pc_UP_700) and the sequence of 700 base pairs at 3' region (ldh1.pc_DOWN_700) of ldh1 gene ORF were also amplified using primers of SEQ ID NOS. 7 and 8, and primers of SEQ ID NOS: 11 and 12.

Meanwhile, to amplify the D-LDH gene, DNA fragments of ldhA(Lb. db) and ldhD(Lb. pl) were prepared using the genomes of *Lactobacillus delbrueckii* and *Lactobacillus plantarum* as a template and primers of SEQ ID NOS. 3 and 4, and primers of SEQ ID NOS: 9 and 10.

Subsequently, An overlapping PCR was conducted using the amplified DNA fragments, ldh.pc_UP_700, ldh.pc_DOWN_700 and ldhA(Lb. db), and primers of SEQ ID NOS. 1 and 6 so as to prepare a δldh.pc-ldhA(Lb. db) cassette. The δldh.pc-ldhA (Lb. db) cassette has a nucleotide sequence homologous to the sequences adjacent to ldh ORF region and D-lactate dehydrogenase is located in the middle of the cassette. Further, ldh1 gene was subjected to the same procedures to prepare a δldh1.pc-ldhD(Lb. pl) cassette. In this regard, each cassette was designed to contain XhoI restriction enzyme site at 5'-end, and SpeI restriction enzyme site at 3'-end.

Because ldh1 and ldh2 genes of *Lactobacillus casei* were very similar to ldh and ldh1 genes of *Lactobacillus paracasei*, respectively, the same primers were used. ldh1.ca_UP_700 and the sequence of 700 base pairs at 3' region (ldh1.ca_DOWN_700) were amplified using the genome of *Lactobacillus casei* as a template and primers of SEQ ID NOs. 1 and 2, and primers of SEQ ID NOS: 5 and 6. the 700 base pairs at 5' region (ldh2.ca_UP_700) and the sequence of 700 base pairs at 3' region (ldh2.ca_DOWN_700) of ldh2 gene ORF were also amplified using primers of SEQ ID NOS. 7 and 8, and primers of SEQ ID NOS: 11 and 12.

Subsequently, An overlapping PCR was conducted using ldh1.ca_UP_700, ldh1.ca_DOWN_700, ldhA(Lb. db) and primers of SEQ ID NOS. 1 and 6 so as to prepare a δldh1.ca-ldhA(Lb. db) cassette. The δldh1.ca-ldhA(Lb. db) cassette has a nucleotide sequence homologous to the sequences adjacent to ldh1 ORF region and D-lactate dehydrogenase is located in the middle of the cassette. Further, ldh2 gene was subjected to the same procedures to prepare a δldh2.ca-ldhD(Lb. pl) cassette.

The sequence of 700 base pairs at 5' region (LGG_02523_UP_700) and the sequence of 700 base pairs at 3' region (LGG_02523 DOWN 700) of LGG_02523 gene ORF were amplified using the genome of *Lactobacillus rhamnosus* as a template and primers of SEQ ID NOS. 13 and 14, and primers of SEQ ID NOS: 17 and 18. The sequence of 700 base pairs at 5' region (LGG_00606_UP_700) and the sequence of 700 base pairs at 3' region (LGG_00606_DOWN_700) of LGG_00606 gene ORF were also amplified using primers of SEQ ID NOS. 19 and 20, and primers of SEQ ID NOS: 23 and 24.

Meanwhile, to amplify the D-LDH gene, DNA fragments of ldhA(Lb. db) and ldhD(Lb. pl) were prepared using the genomes of *Lactobacillus delbrueckii* and *Lactobacillus plantarum* as a template and primers of SEQ ID NOS. 15 and 16, and primers of SEQ ID NOS: 21 and 22.

Subsequently, An overlapping PCR was conducted using the amplified DNA fragments, LGG_02523_UP_700, LGG_02523_DOWN_700, ldhA(Lb. db) and primers of SEQ ID NOs. 13 and 18 so as to prepare a δLGG_02523-ldhA(Lb. db) cassette. The δLGG_02523-ldhA(Lb. db) cassette has a nucleotide sequence homologous to LGG_02523 ORF region and D-lactate dehydrogenase is located in the middle of the cassette. Further, LGG_00606 gene was subjected to the same procedures to prepare a δLGG_00606-ldhD(Lb. pl) cassette. In this regard, each cassette was designed to contain XhoI restriction enzyme site at 5'-end, and SpeI restriction enzyme site at 3'-end.

Subsequently, each of 6 types of the cassettes was cloned using XhoI and SpeI restriction enzyme sites into a heat-sensitive vector, pG+host6 which is characterized in that it contains ampicillin- and erythromycin-resistant genes and thus is used as a shuttle vector of *E. coli*-Lactic acid bacteria, and it is not amplified in *Lactobacillus* at 42° C. Therefore, 6 types of vectors, pG+host6-δldh.pc-ldhA(Lb. db) and pG+host6-δldh1.pc-ldhD(Lb. pl), pG+host6-δldh1.ca-ldhA (Lb. db) and pG+host6-δldh2.ca-ldhD(Lb. pl), and pG+host6-δLGG_02523-ldhA(Lb. db) and pG+host6-δLGG_00606-ldhD(Lb. pl) were prepared.

Example 4: Preparation of Transformants

*Lactobacillus paracasei, Lactobacillus casei* or *Lactobacillus rhamnosus* strains cultured in MRS solid media for one day were inoculated in 10 ml of MRS media, followed by stationary culture at 37° C. for one day. 50 ml of MRS was put in 50 ml of tube, and 500 µl of each strain cultured for one day was inoculated thereto, followed by stationary culture at 37° C. for 3 hours and 30 minutes. When OD600 reached 0.8, the culture broths were placed in an ice bath for 5 minutes. Thereafter, the media were removed from the culture broths by centrifugation to obtain the only strains. The strains were washed with a washing buffer (5 mM sodium phosphate, 1 mM MgCl$_2$, pH 7.4) twice. Subsequently, 25 µl of 0.5 M sucrose solution was added to the strains, followed by suspension. Each 50 μl thereof was dispensed. Each 200 ng of the vectors prepared in Examples 3 were added to the strains, followed by electroporation under the conditions of 1800 v, 25 F and 200Ω. Thereafter, the strains were cultured in 500 μl of MRS at 37° C. for 2 hours, and then spread on MRS solid media (MRSE) containing 10 μg/ml of erythromycin, and cultured at 30° C. for 3 days to obtain colonies.

Example 5: Preparation of D-ldh-Inserted Strain

A portion of the colonies obtained from the transformant derived from Lactobacillus paracasei (Lactobacillus strain introduced with a pG+host6-δldh1-ldhA plasmid containing Lactobacillus delbrueckii-derived ldhA) among the colonies obtained in Example 4 was inoculated in 1 ml of liquid MRS media containing 10 μg/ml of erythromycin, followed by stationary culture at 42° C. for one day for induction of primary crossover. 100 μl of the culture broth was spread on solid MRSE media, and incubated for 7 days to obtain colonies. Each single colony was subcultured on solid MRSE media at 42° C. for 2 days. Each of the obtained strains was inoculated in 1.5 ml tube containing 1 ml of MRS, followed by stationary culture at 37° C. for one day for induction of secondary crossover. A portion of the strain cultured at 37° C. was subjected to colony PCR to examine insertion of ldhA(Lb. db) gene at ldh1 region, and single colonies were selected on solid MRS media. Single colonies were subjected to PCR to examine deletion of ldh gene and insertion of D-lactate dehydrogenase, and finally, a ldh1::ldhA(Lb. db) strain was prepared. This strain was used as a parent strain, and ldh deletion and ldhD(Lb. pl) insertion were conducted in the same manner to prepare a final D-lactic acid-producing strain, in which two types of L-lactate dehydrogenase were deleted.

Meanwhile, Lactobacillus casei and Lactobacillus rhamnosus were subjected to the same procedures to prepare D-lactic acid-producing strains, in which two types of L-lactate dehydrogenase were deleted.

Comparative Example 1: Test of Lactic Acid Fermentation of Novel Modified D-Type Lactobacillus Fermentation results between the novel modified D-type Lactobacillus which was prepared in the present invention and 2 types of the known recombinant D-lactic acid-producing strains based on Lb. plantarum. In this regard, the known recombinant D-lactic acid-producing strain based on Lb. plantarum is a strain in which any one or both of 2 types of its own L-lactate dehydrogenase was/were deleted, and it was prepared by a similar method of the paper published by Okano et al. (Appl. Environ. Microbiol. (2009) 462~467). These strains have ldhL1 or ldhL2 gene deletion, and produce D-lactic acid with optical purity of 99% or higher.

In a specific comparative experiment, 2 types of Lactobacillus plantarum-based D-lactic acid-producing strains and novel 3 types of recombinant Lactobacillus strains were cultured on solid MRS media for one day, and each one loop of the obtained cells was inoculated in liquid MRS, followed by culture at 37° C. for one day. Total 5 types of recombinant Lactobacillus strains were inoculated in 250 ml-baffle flask containing 25 ml of GY liquid media with initial cell optical density of 0.1 at 600 nm. The experiment was carried out in an incubator at a temperature of 37° C. with shaking at 100 rpm. Total culture time was 42 hours. The culture broth samples were collected at an initial inoculation time and a final fermentation time, and a proper amount thereof was centrifuged to obtain the supernatant, followed by HPLC. As a result, the initial glucose concentration was 53 g/l. The data analyzed were the average of the results from the experiments repeated twice. The results are summarized in the following Table 3. Enzymatic quantification showed that lactic acid produced in all the samples was optically pure D-lactic acid (Lactic acid, R-Biopharm, Germany).

TABLE 3

Comparison of lactic acid productivity between strains

| Strain | Yield (%) | Productivity (g/l · h) | Sugar Consumption (g/l) | L-lactic acid (g/l) | D-lactic acid (g/l) |
|---|---|---|---|---|---|
| Lb. plantarum ΔldhL1 | 81 | 0.81 | 42 | 0 | 34 |
| Lb. plantarum ΔldhL1 ΔldhL2 | 75 | 0.69 | 39 | 0 | 29 |
| Lb. paracasei ldh::ldhA ldh1::ldhD | 93 | 1.2 | 53 | 0 | 49 |
| Lb. casei ldh1::ldhA ldh2::ldhD | 89 | 1.1 | 53 | 0 | 47 |
| Lb. rhamnosus LGG_02523::ldhA LGG_00606::ldhD | 85 | 0.99 | 49 | 0 | 42 |

As shown in Table 3, it was found that 3 types of the novel recombinant Lactobacillus strains prepared in the present invention had higher yield, productivity and production amount of D-lactic acid than the known strains (Lb. plantarum ΔldhL1 and Lb. plantarum ΔldhL1 ΔldhL2) in which any one or both of 2 types of their own L-lactate dehydrogenase was/were deleted. In particular, it was found that the transformant derived from Lactobacillus paracasei (Lb. paracasei ldh::ldhA ldh1::ldhD) had the highest yield, productivity and production amount of D-lactic acid.

Accordingly, the present inventors designated the transformant (Lb. paracasei ldh::ldhA ldh1::ldhD) as Lactobacillus paracasei CC02-0095. The transformant, which was modified by substituting the polynucleotide encoding LDH (SEQ ID NO: 25) and the polynucleotide encoding LDH1 (SEQ ID NO: 26) of Lactobacillus paracasei with the polynucleotide encoding LDHA (SEQ ID NO: 31) of Lactobacillus delbrueckii and the polynucleotide encoding LDHD (SEQ ID NO: 32) of Lactobacillus plantarum, was the most excellent in terms of yield, productivity, and production amount of the D-lactic acid and. The transformant was deposited with the Korean Culture Center of Microorganisms (hereinafter, abbreviated to "KCCM", under the Budapest Treaty) on Apr. 2, 2012 under Accession No. KCCM11273P.

It will be apparent to those skilled in the art that various modifications and changes may be made without departing from the scope and spirit of the invention. Therefore, it should be understood that the above embodiment is not limitative, but illustrative in all aspects. The scope of the invention includes not only the appended claims but also all changes and modifications of metes and bounds of the claims, or equivalents.

EFFECT OF THE INVENTION

The D-lactic acid-producing strain of the present invention is prepared from an L-lactic acid-producing strain having excellent lactic acid productivity, and thus it has excellent D-lactic acid productivity. Therefore, the strain can be widely used to improve the productivity of various products which are manufactured using D-lactic acid as a raw material.

What is claimed is:

1. A D-lactic acid-producing strain modified to attenuate or inactivate L-lactate dehydrogenase (L-LDH) activity and to enhance D-lactate dehydrogenase (D-LDH) activity, wherein the D-lactic acid-producing strain so modified is a *Lactobacillus* sp strain which produces more L-lactic acid than D-lactic acid prior to said modification; wherein the L-LDH activity is derived from a L-LDH-encoding polynucleotide from *Lactobacillus paracasei, Lactobacillus casei,* or *Lactobacillus rhamnosus*; wherein the D-LDH activity is derived from a D-LDH-encoding polynucleotide from *Lactobacillus plantarum* or *Lactobacillus delbrueckii*; and wherein the *Lactobacillus* sp. strain is selected from the group consisting of *Lactobacillus casei, Lactobacillus paracasei,* and *Lactobacillus rhamnosus.*

2. The strain according to claim 1, wherein the L-LDH-encoding polynucleotide is selected from the group consisting of ldh (SEQ ID NO: 25) and ldh1 (SEQ ID NO: 26) of *Lactobacillus paracasei*, ldh1 (SEQ ID NO: 27) and ldh2 (SEQ ID NO: 28) of *Lactobacillus paracasei*, and ldh (LGG_02523) (SEQ ID NO: 29) and ldh (LGG_00606) (SEQ ID NO: 30) of *Lactobacillus rhamnosus.*

3. The strain according to claim 1, wherein the D-LDH-encoding polynucleotide is from *Lactobacillus plantarum* or *Lactobacillus delbrueckii*.

4. The strain according to claim 3, wherein the D-LDH-encoding polynucleotide is a LDHA (SEQ ID NO: 31)-encoding polynucleotide from *Lactobacillus delbrueckii* or a LDHD (SEQ ID NO: 32)-encoding polynucleotide from *Lactobacillus plantarum*.

5. The strain according to claim 1, wherein one or more heterogenous D-LDH-encoding polynucleotides are substituted for the L-LDH-encoding polynucleotide in the chromosome and are overexpressed.

6. The strain according to claim 2, wherein the polynucleotide encoding LDH1 (SEQ ID NO: 27) and the polynucleotide encoding LDH2 (SEQ ID NO: 28) of *Lactobacillus casei* are substituted with a polynucleotide encoding LDHA (SEQ ID NO: 31) of *Lactobacillus delbrueckii* and a polynucleotide encoding LDHD (SEQ ID NO: 32) of *Lactobacillus plantarum*, respectively.

7. The strain according to claim 2, wherein the polynucleotide encoding LDH (SEQ ID NO: 25) and the polynucleotide encoding LDH1 (SEQ ID NO: 26) of *Lactobacillus paracasei* are substituted with a polynucleotide encoding LDHA (SEQ ID NO: 31) of *Lactobacillus delbrueckii* and a polynucleotide encoding LDHD (SEQ ID NO: 32) of *Lactobacillus plantarum*, respectively.

8. The strain according to claim 2, wherein the polynucleotide encoding LDH(LGG_02523) (SEQ ID NO: 29) and the polynucleotide encoding LDH(LGG_00606) (SEQ ID NO: 30) of *Lactobacillus rhamnosus* are substituted with a polynucleotide encoding LDHA (SEQ ID NO: 31) of *Lactobacillus delbrueckii* and a polynucleotide encoding LDHD (SEQ ID NO: 32) of *Lactobacillus plantarum*, respectively.

9. The strain according to claim 7, wherein the polynucleotide of *Lactobacillus paracasei* are from *Lactobacillus paracasei* CCO2-0095 deposited under Accession No. KCCM11273P.

10. A method for preparing a modified D-lactic acid-producing strain, comprising:
  (a) attenuating or inactivating L-lactate dehydrogenase (L-LDH) activity in an L-lactic acid-producing strain to obtain a modified lactic acid-producing strain; and
  (b) introducing or enhancing D-lactate dehydrogenase (D-LDH) activity in the modified lactic acid-producing strain,
  wherein the D-lactic acid-producing strain so modified is a *Lactobacillus* sp strain which produces more L-lactic acid than D-lactic acid prior to said modification; wherein the L-LDH activity is derived from a L-LDH-encoding polynucleotide from *Lactobaccillus paracasei, Lactobacillus casei*, or *Lactobacillua rhamnosus*; wherein the D-LDH activity is derived from a D-LDH-encoding polynucleotide from *Lactobacillus plantarum* or *Lactobacillus delbrueckii*; and wherein the *Lactobacillus* sp. strain is selected from the group consisting of *Lactobacillus casei, Lactobaccillus paracasei*, and *Lactobacillus rhamnosus*.

11. The method according to claim 10, wherein the L-LDH activity is attenuated or inactivated by substitution, deletion, insertion or addition of an L-LDH-encoding polynucleotide and the L-LDH-encoding polynucleotide is selected from the group consisting of ldh (SEQ ID NO: 25) and ldh1 (SEQ ID NO: 26) of *Lactobacillus paracasei*, ldh1 (SEQ ID NO: 27) and ldh2 (SEQ ID NO: 28) of *Lactobacillus casei*, ldh(LGG_02523) (SEQ ID NO: 29) and ldh (LGG_00606). (SEQ ID NO: 30) of *Lactobacillus rhamnosus*.

12. A method for producing D-lactic acid, comprising:
  (a) culturing the modified D-lactic acid-producing strain of claim 1 to obtain a culture broth; and
  (b) recovering D-lactic acid from the culture broth.

13. A method for producing D-lactic acid, comprising:
  (a) culturing the modified D-lactic acid-producing strain of claim 2 to obtain a culture broth; and
  (b) recovering D-lactic acid from the culture broth.

14. A method for producing D-lactic acid, comprising:
  (a) culturing the modified D-lactic acid-producing strain of claim 3 to obtain a culture broth; and
  (b) recovering D-lactic acid from the culture broth.

15. A method for producing D-lactic acid, comprising:
  (a) culturing the modified D-lactic acid-producing strain of claim 6 to obtain a culture broth; and
  (b) recovering D-lactic acid from the culture broth.

16. A method for producing D-lactic acid, comprising:
  (a) culturing the modified D-lactic acid-producing strain of claim 7 to obtain a culture broth; and
  (b) recovering D-lactic acid from the culture broth.

17. A method for producing D-lactic acid, comprising:
  (a) culturing the modified D-lactic acid-producing strain of claim 9 to obtain a culture broth; and
  (b) recovering D-lactic acid from the culture broth.

18. A method for producing D-lactic acid, comprising:
  (a) culturing the modified D-lactic acid-producing strain of claim 10 to obtain a culture broth; and
  (b) recovering D-lactic acid from the culture broth.

19. A method for producing D-lactic acid, comprising:
  (a) culturing the modified D-lactic acid-producing strain of claim 11 to obtain a culture broth; and
  (b) recovering D-lactic acid from the culture broth.

20. A method for producing D-lactic acid, comprising:
  (a) culturing the modified D-lactic acid-producing strain of claim 12 to obtain a culture broth; and
  (b) recovering D-lactic acid from the culture broth.

21. A method for producing D-lactic acid, comprising:
  (a) culturing the modified D-lactic acid-producing strain of claim 13 to obtain a culture broth; and
  (b) recovering D-lactic acid, from the culture broth.

* * * * *

SEQUENCE LISTING

<160> NUMBER OF SEQ ID NOS: 32

<210> SEQ ID NO 1
<211> LENGTH: 37
<212> TYPE: DNA
<213> ORGANISM: Artificial Sequence
<220> FEATURE:
<223> OTHER INFORMATION: primer

<400> SEQUENCE: 1
atatgcctcg agcgggattt cctaggccaa caatcat        37

<210> SEQ ID NO 2
<211> LENGTH: 50
<212> TYPE: DNA
<213> ORGANISM: Artificial Sequence
<220> FEATURE:
<223> OTHER INFORMATION: primer

<400> SEQUENCE: 2
ttgcgtaagc aaaaatttta gtcatggtga tatcatcctt tcttatgtgc        50

<210> SEQ ID NO 3
<211> LENGTH: 50
<212> TYPE: DNA
<213> ORGANISM: Artificial Sequence
<220> FEATURE:
<223> OTHER INFORMATION: primer

<400> SEQUENCE: 3
gcacataaga aaggatgata tcaccatgac taaaattttt gcttacgcaa        50

<210> SEQ ID NO 4
<211> LENGTH: 55
<212> TYPE: DNA
<213> ORGANISM: Artificial Sequence
<220> FEATURE:
<223> OTHER INFORMATION: primer

<400> SEQUENCE: 4
tggttgctta cttatcagtg atcgtgatga ttagccaacc ttaactggag tttca        55

<210> SEQ ID NO 5
<211> LENGTH: 55
<212> TYPE: DNA
<213> ORGANISM: Artificial Sequence
<220> FEATURE:
<223> OTHER INFORMATION: primer

<400> SEQUENCE: 5
tgaaactcca gttaaggttg gctaatcatc acgatcactg ataagtaagc aacca        55

<210> SEQ ID NO 6
<211> LENGTH: 39
<212> TYPE: DNA
<213> ORGANISM: Artificial Sequence
<220> FEATURE:
<223> OTHER INFORMATION: primer

<400> SEQUENCE: 6
atatgcacta gtgcttgtta aggatttgtg tcaagcctt        39

<210> SEQ ID NO 7
<211> LENGTH: 35
<212> TYPE: DNA
<213> ORGANISM: Artificial Sequence

```
<220> FEATURE:
<223> OTHER INFORMATION: primer

<400> SEQUENCE: 7
atctctcgag tctgacttac ctttcggatc aaaat                              35

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
ctcaaattcc tcctcatgaa gatct                                        25

<210> SEQ ID NO 9
<211> LENGTH: 50
<212> TYPE: DNA
<213> ORGANISM: Artificial Sequence
<220> FEATURE:
<223> OTHER INFORMATION: primer

<400> SEQUENCE: 9
cgtcaagatc ttcatgagga ggaatttgag atgaaaatta ttgcatatgc              50

<210> SEQ ID NO 10
<211> LENGTH: 50
<212> TYPE: DNA
<213> ORGANISM: Artificial Sequence
<220> FEATURE:
<223> OTHER INFORMATION: primer

<400> SEQUENCE: 10
ccgttaagct gagcgcttaa cctgacgagc ttagtcaaac ttaacttgcg              50

<210> SEQ ID NO 11
<211> LENGTH: 25
<212> TYPE: DNA
<213> ORGANISM: Artificial Sequence
<220> FEATURE:
<223> OTHER INFORMATION: primer

<400> SEQUENCE: 11
gctcgtcagg ttaagcgctc agctt                                        25

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
atatactagt ccgttggctg ggcattgcgt cattc                             35

<210> SEQ ID NO 13
<211> LENGTH: 35
<212> TYPE: DNA
<213> ORGANISM: Artificial Sequence
<220> FEATURE:
<223> OTHER INFORMATION: primer

<400> SEQUENCE: 13 cccccctcgag ctggtaatac atcattaact gccgc                            35
```

<210> SEQ ID NO 14
<211> LENGTH: 50
<212> TYPE: DNA
<213> ORGANISM: Artificial Sequence
<220> FEATURE:
<223> OTHER INFORMATION: primer

<400> SEQUENCE: 14
ttgcgtaagc aaaaatttta gtcatggtga tatcatcctt tcttatgtgc      50

<210> SEQ ID NO 15
<211> LENGTH: 50
<212> TYPE: DNA
<213> ORGANISM: Artificial Sequence
<220> FEATURE:
<223> OTHER INFORMATION: primer

<400> SEQUENCE: 15
gcacataaga aaggatgata tcaccatgac taaaattttt gcttacgcaa      50

<210> SEQ ID NO 16
<211> LENGTH: 50
<212> TYPE: DNA
<213> ORGANISM: Artificial Sequence
<220> FEATURE:
<223> OTHER INFORMATION: primer

<400> SEQUENCE: 16
ggtttaaaat cagttatggt gaagattagc caaccttaac tggagtttca      50

<210> SEQ ID NO 17
<211> LENGTH: 50
<212> TYPE: DNA
<213> ORGANISM: Artificial Sequence
<220> FEATURE:
<223> OTHER INFORMATION: primer

<400> SEQUENCE: 17
tgaaactcca gttaaggttg gctaatcttc accataactg attttaaacc      50

<210> SEQ ID NO 18
<211> LENGTH: 35
<212> TYPE: DNA
<213> ORGANISM: Artificial Sequence
<220> FEATURE:
<223> OTHER INFORMATION: primer

<400> SEQUENCE: 18
tagaactagt ttattcagca cttgagtaag tcctt      35

<210> SEQ ID NO 19
<211> LENGTH: 35
<212> TYPE: DNA
<213> ORGANISM: Artificial Sequence
<220> FEATURE:
<223> OTHER INFORMATION: primer

<400> SEQUENCE: 19 cccccctcgag aaccaagcgt ccaagaatgt ttgct      35

<210> SEQ ID NO 20
<211> LENGTH: 50
<212> TYPE: DNA
<213> ORGANISM: Artificial Sequence
<220> FEATURE:
<223> OTHER INFORMATION: primer

<400> SEQUENCE: 20
gtacagcata tgcaataatt ttcatcctaa acccctcctt gacaggtagc        50

<210> SEQ ID NO 21
<211> LENGTH: 50
<212> TYPE: DNA
<213> ORGANISM: Artificial Sequence
<220> FEATURE:
<223> OTHER INFORMATION: primer

<400> SEQUENCE: 21
gctacctgtc aaggaggggt ttaggatgaa aattattgca tatgctgtac        50

<210> SEQ ID NO 22
<211> LENGTH: 50
<212> TYPE: DNA
<213> ORGANISM: Artificial Sequence
<220> FEATURE:
<223> OTHER INFORMATION: primer

<400> SEQUENCE: 22
aaaaatactg acgatgggtt gtgttttagt caaacttaac ttgcgtatca        50

<210> SEQ ID NO 23
<211> LENGTH: 50
<212> TYPE: DNA
<213> ORGANISM: Artificial Sequence
<220> FEATURE:
<223> OTHER INFORMATION: primer

<400> SEQUENCE: 23
tgatacgcaa gttaagtttg actaaaacac aacccatcgt cagtattttt        50

<210> SEQ ID NO 24
<211> LENGTH: 35
<212> TYPE: DNA
<213> ORGANISM: Artificial Sequence
<220> FEATURE:
<223> OTHER INFORMATION: primer

<400> SEQUENCE: 24
tagaactagt caaccgttgt cgaaagcatt gcggt                        35

<210> SEQ ID NO 25
<211> LENGTH: 981
<212> TYPE: DNA
<213> ORGANISM: Lactobacillus paracasei ldh

<400> SEQUENCE: 25
gtggcaagta ttacggataa ggatcaccaa aaagttattc tcgttggtga cggcgccgtt     60
ggttcaagtt atgcctacgc aatggttttg caaggtatcg ctcaggaaat cggaatcgtt    120
gacattttca aggacaagac aaagggtgac gcgattgact tgagcaacgc gctcccattc    180
acaagtccta agaagattta ttcagctgaa tacagcgatg ctaaggatgc tgatctggtt    240
gttatcacag ctggcgctcc tcagaagcct ggcgaaactc gtttggactt ggttaacaag    300
aacttgaaga tcttgaagtc cattgttgac ccaatcgttg attccggctt taacggtatt    360
ttcttagttg ctgccaaccc agttgacatt tgacctatg caacttggaa actttctggc    420
ttcccgaaga accggttgt tggttccggt acttcactgg acaccgcccg cttccgtcag    480
tccattgctg aaatggttaa tgttgacgct cgttcggtcc acgcttacat catgggcgaa    540

```
catggtgaca ctgaattccc tgtatggtcc cacgctaaca ttggtggcgt taccatcgct      600
gaatgggtta aggctcatcc agaaatcaag gaagacaagc ttgttaagat gtttgaagac      660
gttcgtgacg ccgcttatga aatcatcaaa ctcaagggtg cgaccttcta tggtatcgca      720
actgcccttg cccggatttc aaaggcaatc cttaacgacg aaaatgcggt tctgccactt      780
tccgtttaca tggatggtca atatggcttg aacgacatct acatcggtac cccagctgtg      840
atcaaccgta tggtatcca gaacatcctg gaaatcccat tgaccgatca cgaagaagaa       900
tccatgcaga aatctgcttc tcaattgaag aaggttctga ccgatgcttt cgctaagaat      960
gacatcgaaa ctcgtcagta a                                                981
```

<210> SEQ ID NO 26
<211> LENGTH: 999
<212> TYPE: DNA
<213> ORGANISM: Lactobacillus paracasei ldh1

<400> SEQUENCE: 26

```
atgaaaatta ttgcatatgc tgtacgtgat gacgaacgtc cattcttcga tacttggatg       60
aaagaaaacc cagatgttga agttaaatta gttccagaat tacttactga agacaacgtt      120
gacttagcta aaggcttcga cggtgccgat gtataccaac aaaaggacta tactgctgaa      180
gtattgaaca gttagccga cgaaggggtt aagaacatct ctcttcgtaa cgttggtgtt      240
gataacttgg acgttcctac tgttaaagca cgtggcttaa acatttctaa cgtacctgca      300
tactcaccaa atgcgattgc tgaattatca gtaacgcaat tgatgcaatt attacgtcaa      360
accccattgt tcaataagaa gttagctaag caagacttcc gttgggcacc agatattgcc      420
aaggaattaa acaccatgac tgttggtgtt atcggtactg tcggattgg ccgtgctgcc      480 atcgatattt tcaaaggctt cggcgctaag gttatcggtt acgatgttta ccggaatgct      540
gaacttgaaa aggaaggcat gtacgttgac accttggacg aattatacgc ccaagctgat      600
gttatcacgt tacacgttcc tgcattgaag ataactacc acatgttgaa tgcggatgcc      660
ttcagcaaga tgaaagatgg cgcctacatc ttgaactttg ctcgtgggac actcatcgat      720
tcagaagact tgatcaaagc cttagacagt ggcaaagttg ccggtgccgc tcttgatacg      780
tatgaatacg aaactaagat cttcaacaaa gaccttgaag gtcaaacgat tgatgacaag      840
gtcttcatga acttgttcaa ccgcgacaat gttttgatta caccacatac ggctttctac      900
actgaaactg ccgttcacaa catggtgcac gtttcaatga acagtaacaa acaattcatc      960
gaaactggta agctgatac gcaagttaag tttgactaa                             999
```

<210> SEQ ID NO 27
<211> LENGTH: 981
<212> TYPE: DNA
<213> ORGANISM: Lactobacillus casei ldh1

<400> SEQUENCE: 27

```
gtggcaagta ttacggataa ggatcaccaa aaagttattc tcgttggtga cggcgccgtt       60
ggttcaagtt atgcctacgc aatggttttg caaggtatcg ctcaggaaat cggaatcgtt      120
gacattttca aggacaagac aaagggtgac gcgattgact tgagcaacgc gctcccattc      180
acaagtccta agaagattta ttcagctgaa tacagcgatg ctaaggatgc tgatctggtt      240
gttatcacag ctggcgctcc tcagaagcct ggcgaaactc gtttggactt ggttaacaag      300
aacttgaaga tcttgaagtc cattgttgac ccaatcgttg attccggctt taacggtatt      360
ttcttagttg ctgccaaccc agttgacatt ttgacctatg caacttggaa actttctggc      420
```

```
ttcccgaaga accgggttgt tggttccggt acttcactgg acaccgcccg cttccgtcag     480
tccattgctg aaatggttaa tgttgacgct cgttcggtcc acgcttacat catgggcgaa     540
catggtgaca ctgaattccc tgtatggtcc cacgctaaca ttggtggcgt taccatcgct     600
gaatgggtta aggctcatcc agaaatcaag gaagacaagc ttgttaagat gtttgaagac     660
gttcgtgacg ccgcttatga aatcatcaaa ctcaagggtg cgaccttcta tggtatcgca     720
actgcccttg cccggatttc aaaggcaatc cttaacgacg aaaatgcggt tctgccactt     780
tccgtttaca tggatggtca atatggcttg aacgacatct acatcggtac cccagctgtg     840
atcaaccgta atggtatcca gaacatcctg gaaatcccat tgaccgatca cgaagaagaa     900
tccatgcaga aatctgcttc tcaattgaag aaggttctga ccgatgcttt cgctaagaat     960
gacatcgaaa ctcgtcagta a                                               981

<210> SEQ ID NO 28
<211> LENGTH: 939
<212> TYPE: DNA
<213> ORGANISM: Lactobacillus casei ldh2

<400> SEQUENCE: 28
atgcggaaca acggcaatat tattttaatt ggtgatggcg cgattggatc aagttatgcg      60
ttcaactgtc tcaccaccgg cgtcggccag agtcttggta ttattgatgt taacgaaaaa     120
cgcgtgcaag gtgacgtcga agatctttct gattccctac cttacgtc acagaagaat       180 atttatgcgg ccagctatga agattgcaaa tatgccgata ttatcgtcat cacagccgga     240
attgcccaaa agccaggtca gacacgccta caacttttgg ccatcaacgc aaagatcatg     300
aaagaaatca cacataacat tatggcaagc gggttcaatg ggtttattct agtcgcatcc     360
aatccagtcg atgtccttgc cgaattagtc ttgcaagaat ccggcttgcc acgtaatcag     420
gtgctgggat cagggacggc gcttgattca gctcgcttac ggtctgagat cggtctgcgt     480
tataacgtgg acgcccggat tgtgcacggc tacatcatgg gtgaacacgg cgattctgaa     540
tttccagttt gggactacac caacattggc ggcaaaccga ttcttgattg gattcctaaa     600
gatcgccagg ataaagatct gcctgatatt gcgagcgcg tcaaaacggc tgcttatggc     660
atcattgaga aaaaggtgc cactttctac ggcattgctg cctcattaac ccgtttaacc     720 agcgcccttct tgaatgatga tcgcgcagca ttcgcaatgt ccgtccattt ggaaggcgaa     780
tacggcttgt caggtgtttc catcggtgta ccggtaatcc tcggcgctaa tggcttagaa     840
cgcatcattg agctggattt gaacccagaa gatcataagc ggttagccga ttctgcagct     900
attttgaaag aaaatctgaa gaaggctcaa gaagcttaa                            939

<210> SEQ ID NO 29
<211> LENGTH: 981
<212> TYPE: DNA
<213> ORGANISM: Lactobacillus rhamnosus LGG_02523

<400> SEQUENCE: 29
gtggcaagta ttacggataa ggatcaccaa aaagttattc tcgttggtga tggcgccgtt      60
ggttcaagct atgcctatgc aatggttttg caaggtatcg ctcaagaaat cgggattgtt     120
gacattttca aggacaagac gaaaggtgac gcaattgatt taagcaacgc gctcccattc     180
accagtccta agaagattta ttctgctgaa tacagcgatg ccaaggatgc tgatctggtt     240
gttatcactg ctggtgctcc tcaaaagcct ggcgaaactc gcttggatct ggttaacaag     300
```

```
aacttgaaga ttttgaagtc cattgttgat ccgatcgtgg attctggctt taacggtatc    360
ttcttggttg ctgctaaccc agttgatatc ttgacttatg ctacttggaa gctttccgga    420
ttcccgaaga gccgggttgt tggttcaggt acttctctgg acaccgctcg tttccgtcaa    480
tccattgctg aaatggttaa cgttgatgct cgttccgtcc acgcatatat catgggtgaa    540
cacggcgaca cagaattccc tgtatggtcc cacgctaaca ttggtggcgt taccatcgct    600
gaatgggtta agcacatcc agaaatcaaa gaagacaaac ttgttaagat gtttgaagac    660
gttcgtgacg ctgcttacga atcatcaaa ctcaagggtg caaccttcta cggtatcgca    720
actgctttgg cacggatttc caaagcaatt cttaacgatg aaaatgcggt actcccattg    780
tccgtttaca tggacggcca atatggcttg aacgacatct acattggtac acctgctgtg    840
atcaaccgca atggtattca gaacattctg gaaatcccat tgaccgacca cgaagaagaa    900
tccatgcaga agtcggcttc acaattgaag aaagttctga ccgatgcgtt tgctaagaac    960
gacatcgaaa cacgtcagta a                                              981

<210> SEQ ID NO 30
<211> LENGTH: 939
<212> TYPE: DNA
<213> ORGANISM: Lactobacillus rhamnosus LGG_00606

<400> SEQUENCE: 30
atgcaacata gcggaaatat tattttaatt ggtgacggcg ctatcggttc gagctttgct     60
tttaactgtt taacgaccgg cgttggtcaa agcctgggca ttattgacgt caatgagaaa    120
cgagtacaag gcgatgtgga ggatctttcg gacgcgctgc cgtatacgtc ccaaaagaat    180
atctatgcag cgagttatga agactgcaaa tacgccgata tcattgtgat cacggctggc    240
atcgcgcaaa agcccggtca gacccgactg gaactgttgt cgatcaatgc caaaatcata    300
aaagaaatca cgcacaatat catggccagt ggttttaatg gttttattct cgttgcctca    360
aacccggtcg acgtgctcgc ggaattagtg ctggaagaat cggggctgcc gcgtaaccaa    420
gtactaggct caggtacagc gctggattca gcccgtctgc gttcggaaat cggcttgcgt    480
tacaatgtgg atgcgcgcat tgtccacggc tacatcatgg cgaacatgg cgactccgaa    540 tttccggttt gggattacac caatattggc ggcaaaccga ttctcgattg gattcccaaa    600
aatcgccaag caagtgattt agctgaaatc agccaccgcg ttaaaactgc cgcatatggc    660
atcattgaaa agaaaggtgc tactttctac ggaatcgccg cttcgctcac ccgcctgacc    720
agtgcctttt tgaatgacga ccgggcagca ttcgcgatgt cggtccatct tgacggtgag    780 tatggttttgt caggtgtctc cattggggta ccggttatcc tcggcgcaaa cggcttagaa    840
cgtatcatcg aacttgattt aaacgcggaa gaccacaaac gcctggctga ctctgctgcc    900
attttgaaag ataatttaaa gaaggcacag gaagcctag                            939

<210> SEQ ID NO 31
<211> LENGTH: 333
<212> TYPE: PRT
<213> ORGANISM: Lactobacillus delbrueckii ldhA

<400> SEQUENCE: 31

Met Thr Lys Ile Phe Ala Tyr Ala Ile Arg Glu Asp Glu Lys Pro Phe
  1               5                  10                  15

Leu Lys Glu Trp Glu Asp Ala His Lys Asp Val Glu Val Glu Tyr Thr
             20                  25                  30

Asp Lys Leu Leu Thr Pro Glu Thr Val Ala Leu Ala Lys Gly Ala Asp
```

```
            35                  40                  45
Gly Val Val Tyr Gln Gln Leu Asp Tyr Thr Ala Glu Thr Leu Gln
 50                  55                  60

Ala Leu Ala Asp Asn Gly Ile Thr Lys Met Ser Leu Arg Asn Val Gly
 65                  70                  75                  80

Val Asp Asn Ile Asp Met Ala Lys Ala Lys Glu Leu Gly Phe Gln Ile
                     85                  90                  95

Thr Asn Val Pro Val Tyr Ser Pro Asn Ala Ile Ala Glu His Ala Ala
                    100                 105                 110

Ile Gln Ala Ala Arg Ile Leu Arg Gln Asp Lys Ala Met Asp Glu Lys
                115                 120                 125

Val Ala Arg His Asp Leu Arg Trp Ala Pro Thr Ile Gly Arg Glu Val
130                 135                 140

Arg Asp Gln Val Val Gly Val Ile Gly Thr Gly His Ile Gly Gln Val
145                 150                 155                 160

Phe Met Gln Ile Met Glu Gly Phe Gly Ala Lys Val Ile Ala Tyr Asp
                165                 170                 175

Ile Phe Arg Asn Pro Glu Leu Glu Lys Lys Gly Tyr Tyr Val Asp Ser
                180                 185                 190

Leu Asp Asp Leu Tyr Lys Gln Ala Asp Val Ile Ser Leu His Val Pro
                195                 200                 205

Asp Val Pro Ala Asn Val His Met Ile Asn Asp Glu Ser Ile Ala Lys
                210                 215                 220

Met Lys Gln Asp Val Val Ile Val Asn Val Ser Arg Gly Pro Leu Val
225                 230                 235                 240

Asp Thr Asp Ala Val Ile Arg Gly Leu Asp Ser Gly Lys Ile Phe Gly
                245                 250                 255

Tyr Ala Met Asp Val Tyr Glu Gly Glu Val Gly Ile Phe Asn Glu Asp
                260                 265                 270

Trp Glu Gly Lys Glu Phe Pro Asp Ala Arg Leu Ala Asp Leu Ile Ala
                275                 280                 285

Arg Pro Asn Val Leu Val Thr Pro His Thr Ala Phe Tyr Thr Thr His
                290                 295                 300

Ala Val Arg Asn Met Val Val Lys Ala Phe Asp Asn Asn Leu Glu Leu
305                 310                 315                 320

Val Glu Gly Lys Glu Ala Glu Thr Pro Val Lys Val Gly
                325                 330

<210> SEQ ID NO 32
<211> LENGTH: 332
<212> TYPE: PRT
<213> ORGANISM: Lactobacillus plantarum ldhD

<400> SEQUENCE: 32

Met Lys Ile Ile Ala Tyr Ala Val Arg Asp Asp Glu Arg Pro Phe Phe
 1                   5                  10                  15

Asp Thr Trp Met Lys Glu Asn Pro Asp Val Glu Val Lys Leu Val Pro
                 20                  25                  30

Glu Leu Leu Thr Glu Asp Asn Val Asp Leu Ala Lys Gly Phe Asp Gly
             35                  40                  45

Ala Asp Val Tyr Gln Gln Lys Asp Tyr Thr Ala Glu Val Leu Asn Lys
         50                  55                  60

Leu Ala Asp Glu Gly Val Lys Asn Ile Ser Leu Arg Asn Val Gly Val
 65                  70                  75                  80
```

```
Asp Asn Leu Asp Val Pro Thr Val Lys Ala Arg Gly Leu Asn Ile Ser
                85              90                  95
Asn Val Pro Ala Tyr Ser Pro Asn Ala Ile Ala Glu Leu Ser Val Thr
            100             105                 110
Gln Leu Met Gln Leu Leu Arg Gln Thr Pro Leu Phe Asn Lys Lys Leu
            115             120                 125
Ala Lys Gln Asp Phe Arg Trp Ala Pro Asp Ile Ala Lys Glu Leu Asn
    130             135             140
Thr Met Thr Val Gly Val Ile Gly Thr Gly Arg Ile Gly Arg Ala Ala
145             150              155                 160
Ile Asp Ile Phe Lys Gly Phe Gly Ala Lys Val Ile Gly Tyr Asp Val
                165             170                 175
Tyr Arg Asn Ala Glu Leu Glu Lys Glu Gly Met Tyr Val Asp Thr Leu
            180             185                 190
Asp Glu Leu Tyr Ala Gln Ala Asp Val Ile Thr Leu His Val Pro Ala
            195             200             205
Leu Lys Asp Asn Tyr His Met Leu Asn Ala Asp Ala Phe Ser Lys Met
    210             215             220
Lys Asp Gly Ala Tyr Ile Leu Asn Phe Ala Arg Gly Thr Leu Ile Asp
225             230             235                 240
Ser Glu Asp Leu Ile Lys Ala Leu Asp Ser Gly Lys Val Ala Gly Ala
            245             250             255
Ala Leu Asp Thr Tyr Glu Tyr Glu Thr Lys Ile Phe Asn Lys Asp Leu
            260             265             270
Glu Gly Gln Thr Ile Asp Asp Lys Val Phe Met Asn Leu Phe Asn Arg
            275             280             285
Asp Asn Val Leu Ile Thr Pro His Thr Ala Phe Tyr Thr Glu Thr Ala
    290             295             300
Val His Asn Met Val His Val Ser Met Asn Ser Asn Lys Gln Phe Ile
305             310             315                 320
Glu Thr Gly Lys Ala Asp Thr Gln Val Lys Phe Asp
            325             330
```